United States Patent [19]
Weng

[11] Patent Number: 5,552,645
[45] Date of Patent: Sep. 3, 1996

[54] AUTOMATIC PROBE ACTIVATION

[75] Inventor: Lee Weng, Issaquah, Wash.

[73] Assignee: Siemens Medical Systems, Inc., Iselin, N.J.

[21] Appl. No.: 255,501

[22] Filed: Jun. 8, 1994

[51] Int. Cl.⁶ .................................................. H01H 35/14
[52] U.S. Cl. ............... 307/117; 128/660.01; 128/660.09; 128/660.1; 307/112; 307/116; 73/861.18; 73/861.25
[58] Field of Search ..................................... 307/117, 116, 307/112; 128/660.01–661.01; 73/570, 623, 625, 633, 861.25, 861.18

[56] References Cited

U.S. PATENT DOCUMENTS

| | | | |
|---|---|---|---|
| 4,649,925 | 3/1987 | Dow et al. | 128/660 |
| 4,852,577 | 8/1989 | Smith et al. | 128/660 |
| 5,085,221 | 2/1992 | Ingebrigtsen et al. | 128/660.1 |
| 5,361,768 | 11/1994 | Weber et al. | 128/660.09 |

Primary Examiner—William M. Shoop, Jr.
Assistant Examiner—Albert W. Paladini

[57] ABSTRACT

Ultrasound imaging system providing automatic activation of a probe, which ultrasound system includes: (a) a motion sensor for detecting motion of the probe and for generating a signal in response to the motion; (b) a signal detector for detecting the signal; and (c) a probe activator, in response to a detector signal from the detector, for activating the probe. In a preferred embodiment of the present invention, the motion sensor is an accelerometer which is affixed to the probe.

6 Claims, 1 Drawing Sheet

AUTOMATIC PROBE ACTIVATION

TECHNICAL FIELD OF THE INVENTION

The present invention relates to method and apparatus for activating a probe and, in particular, for activating a probe used with an ultrasound imaging system.

BACKGROUND OF THE INVENTION

As is well known in the art, ultrasound imaging systems have one or more probes. In systems having more than one probe, there must be a technique for providing an indication that a particular probe will be used by a sonographer. One existing technique for providing an indication uses switch activated control circuits, which circuits are activated manually by, for example, pressing a button on a console, to indicate that a particular probe is in use. Then, in response to the indication generated when the user presses the button, the ultrasound system activates the indicated probe in a manner which is well known in the art. Aother existing technique for providing an indication uses probe holders which contain switches that are activated when a probe is removed from its holder. When a switch is activated, an indication is provided which causes the ultrasound system to activate the probe. Still another existing technique for providing an indication uses switch activated control circuits, which circuits are activated manually by, for example, pressing a button disposed on the probe to indicate that a particular probe is in use.

There are disadvantages associated with each of the above-described techniques. The first technique is disadvantageous because it requires a user to press a button to indicate that a particular probe is to be activated. The second technique is disadvantageous in that it requires a probe to be returned to its holder before another probe can be used. In addition, for proper activation using the second technique, probes must be returned to specific holders, otherwise the wrong probe will be activated. The third technique is disadvantageous in that it requires the user to remember to press the button to turn the probe on and off.

In light of the above, there is a need in the art for method and apparatus for activating a probe which overcomes the above-described problems.

SUMMARY OF THE INVENTION

Advantageously, embodiments of the present invention are method and apparatus for activating a probe automatically. In particular, an embodiment of the present invention is an ultrasound imaging system providing automatic activation of a probe, which ultrasound system comprises: (a) motion sensor means for detecting motion of the probe and for generating a signal in response to the motion; (b) signal detecting means for detecting the signal; and (c) probe activating means, in response to a detection signal from the detecting means, for activating the probe. In a preferred embodiment of the present invention, the motion sensor means is an accelerometer which is affixed to the probe.

DETAILED DESCRIPTION

Figure 1:
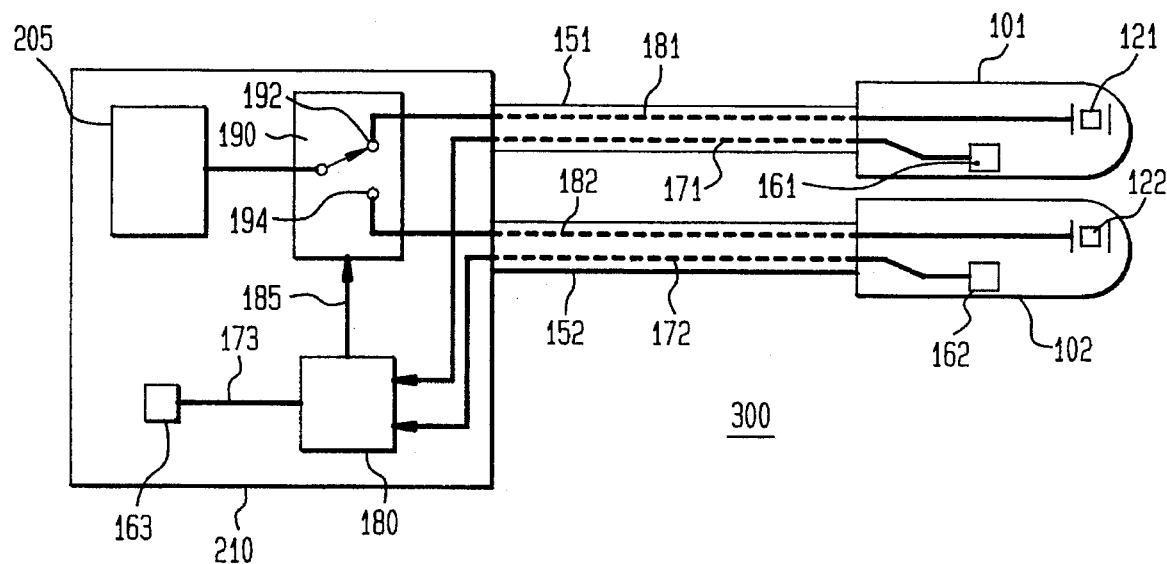
FIG. 1 shows, in pictorial form, an ultrasound imaging system which automatically activates an ultrasound probe in accordance with the present invention.

FIG. 1 shows ultrasound imaging system 300 which automatically activates ultrasound probes 101 and 102 in accordance with the present invention. As shown in FIG. 1: (a) ultrasound probes 101 and 102 are connected to main control station 210 of ultrasound imaging system 300 by cables 151 and 152, respectively; (b) sensors 161 and 162 are affixed to ultrasound probes 101 and 102, respectively; (c) ultrasound transducers 121 and 122 are disposed within ultrasound probes 101 and 102, respectively; (d) communications channel 171 extends from sensor 161, through cable 15 1, to signal detector 180 in main control station 210; (e) communications channel 172 extends from sensor 162, through cable 152, to signal detector 180 in main control station 210; (f) sensor 163 is affixed to main control station 210; and (g) communications channel 173 extends from sensor 163 to signal detector 180. Lastly, signal detector 180 is connected to activation switch 190 by communications link 185 and activation switch 190 interconnects ultrasound transducers 121 or 122 with imaging channel 205 by means of communications links 181 and 182, respectively.

In accordance with the present invention, sensor 161 detects motion of probe 101 and sensor 162 detects motion of probe 102. For example, in response to movement of probe 101, sensor 161 transmits a signal over communications channel 171 to signal detector 180. In response to the signal received from sensor 161, in a manner which will be explained in detail below, signal detector 180 determines that probe 101 is to be activated. Then, signal detector 180 transmits such information over communications link 185 to activation switch 190. Finally, in response to the information received from signal detector 180, activation switch 190 activates probe 101 by connecting probe 101 with imaging channel 205 in accordance with methods which are well known to those of ordinary skill in the art, such as, for example, by use of relay switches.

In a preferred embodiment of the present invention, sensors 161 and 162 are accelerometers which are placed, for example, within the handle of probes 101 and 102. Thus, for example, whenever a user picks up probe 101, sensor 161 (accelerometer 161) generates a signal which is transmitted to signal detector 180, all of which takes place in a manner which is well known to those of ordinary skill in the art.

In embodiments of the present invention wherein ultrasound imaging system 300 has several probes, signal detector 180 is fabricated to distinguish among signals coming from the probes. This ability to distinguish arises, in part, by: (a) routing signals arriving from different probes to different hardware appearances; (b) requiring signals from different probes to be different; or (c) requiring signals to contain identifying information which is embedded within the signals. This information is then used, in the manner which will be described in detail below, to determine which probe is to be activated. This information is then transmitted to activation switch 190. In response, activation switch 190 connects the identified probe to imaging channel 205 to activate the identified probe.

Figure 2:
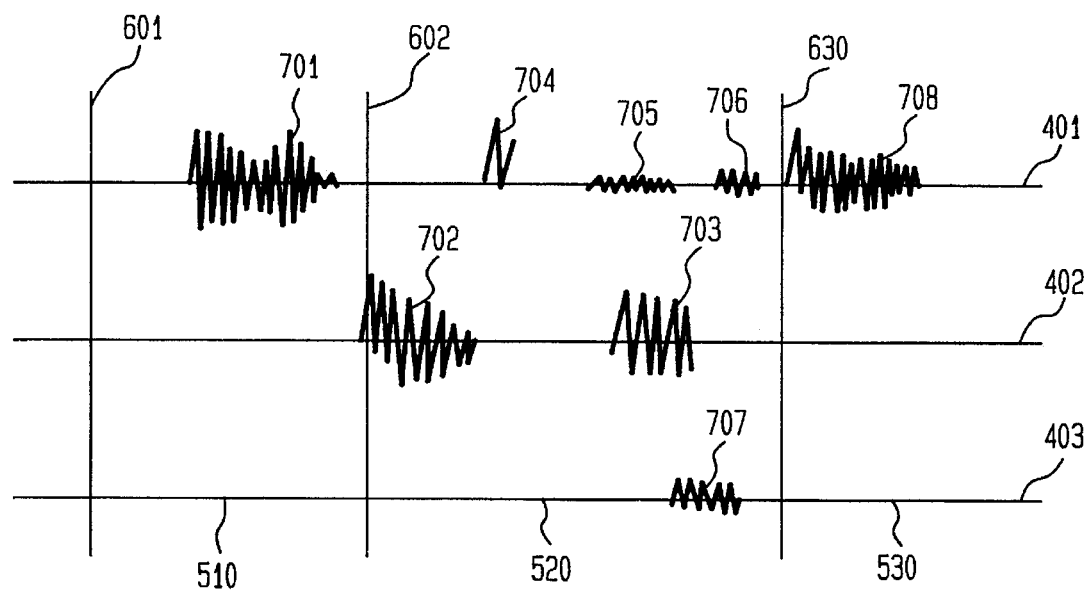
FIG. 2 shows, in graphical form, signals produced by various parts of the ultrasound imaging system shown in FIG, 1.

In a preferred embodiment of the present invention, sensor 163 is affixed to main control station 210 to enable the system to identify motion of probes which is caused by motion of the main control station when the probes are attached thereto. Further, in accordance with the preferred embodiment, signal detector 180 is fabricated to identify other events which are not caused by a user. FIG. 2 shows, in graphical form, signals produced by various parts of ultrasound imaging system 300 shown in FIG. 1. Line 401 shows signals generated by sensor 161, line 402 shows signals generated by sensor 162, and line 403 shows signals generated by sensor 163—all as a function of time.

The following describes the operation of the preferred embodiment of the present invention in conjunction with FIG. 2. Assume that imaging system 300 is turned on at time 601 and that probe 101 is selected for activation as a default condition. Thus, in the default condition, activation switch 190 is set at position 192 (see FIG. 1) so that probe 101 is connected to imaging channel 205. During time interval 510, sensor 161 generates signal 701 when probe 101 is picked up by a user and is moved during subsequent use. Signal 701 is sent through communications channel 171 to signal detector 180. In response to signal 701, signal detector 180 identifies the user-selected probe to be probe 101. Since this matches the probe used for the default condition, signal detector 180 sends no action command to activation switch 190. During time interval 510 probe 101 is always activated and is the only probe which is connected to imaging channel 205.

Time interval 510 ends at time 602 when the user picks up probe 102. At that moment, sensor 162 in probe 102 generates signal 702 which is sent through communications channel 172 to signal detector 180. In response to signal 702, signal detector 180 identifies the user-selected probe to be probe 102 and signal detector 180 sends an action command through communications link 185 to activation switch 190. In response to this action command, activation switch 190 changes the position of the switch from position 192 to position 194 so that probe 102 is now connected to imaging channel 205. Note that typical probe-in-motion signals, such as signals 701 and 703, have relatively large amplitude and relatively long duration.

Time interval 520 starts at time 602 and probe 102 is the only probe which is connected to imaging channel 205 during this time interval. During time interval 520, probe 102 may be picked up and put down and picked up again several times. This will cause sensor 162 to generate and send multiple signals, like signal 703, to signal detector 180. However, as long as such signals are associated with the current probe selection, signal detector 180 will not send action commands to activation switch 190.

While probe 102 is in use during interval 520, sensor 161 in probe 101 may generate some short spike signals like signal 704 and low-level signals like signal 705. Such signals may be generated for unintentional reasons such as, for example, the user accidentally touching the probe or small vibrations in the area where the probe rests. As can be seen in FIG. 2, these signals have significantly different characteristics from probe-in-motion signals 701, 702, and 703 which are generated when a probe is in use by an operator. In the preferred embodiment, signals such as 704 and 705 are filtered by signal detector 180.

During interval 520, unused probe 101 may be placed in a probe holder on main control station 210. Further, the user may adjust the position of main control station 210 while using probe 102. In such an event, movement of main control station 210 causes sensor 161 in probe 101 to generate signal 706 which is similar to signals 701, 702 and 703 which indicate use of a probe by an operator. Sensor 163 is installed on main control station 210 to prevent false probe activation in this case as follows. During motion of main control station 210, sensor 163 generates signal 707, which signal 707 is sent to signal detector 180. Signal detector 180 identifies the coincidence of signals 706 and 707 as being caused by motion of main control station 210 and sends no activation command to activation switch 190. As a result, signal detector 180 ignores signals caused by motion of main control station 210.

Time interval 520 ends and time interval 530 begins at time 630 when the user picks up probe 101 again. During time interval 530, sensor 161 generates signal 708 which indicates that probe 101 is in use. In response, signal detector 180 sends an action command to activation switch 190 to change the switch position from 194 back to 192. Now probe 101 is back in use in time interval 530. As one can readily appreciate from the above, the automatic probe activation process repeats itself by switching back and forth between probes 101 and 102 as the user operates ultrasound imaging system 300.

In summary, in accordance with the preferred embodiment of the present invention, signal detector 180 utilizes the following rules in analyzing signals generated by sensors 161–163 to determine which probe is to activated: (a) if a probe is activated, maintain it in that state until a motion signal is received from another probe; (b) if a motion signal is received from a probe and from sensor 163, do not activate the probe since the main control station has moved, thereby causing the motion signal from the probe; and (c) ignore short, transient signals and low-level signals from an inactive probe. Signal detector 180 is fabricated utilizing a microprocessor or logic for implementing the above-identified rules in a manner which is well known to those of ordinary skill in the art.

As one can readily appreciate, embodiments of the present invention solve the above-identified disadvantages of prior art systems in that a user does not have to press a button to activate or deactivate a probe; a user does not have to place a probe in a holder before picking up another probe; and a user does not have to place a probe in a pre-defined holder.

Note that the present invention is not limited to the embodiment described above. For example, signals generated by motion detectors 161 and 162 to indicate movement of probes 101 and 102, respectively, need not be transmitted by communications channels 171 and 172, respectively, which pass through cables 151 and 152, respectively. In other embodiments of the present invention such signals may be transmitted by broadcast methods of cordless transmission, much like the manner in which information is transmitted by a cordless telephone. In such a mode, the signal would also transmit information which identifies the probe being used.

Although various minor modifications may be suggested by those versed in the art, it should be understood that we wish to embody within the scope of the patent granted hereon all such modification as reasonably and properly come within the scope of our contribution to the art.

What is claimed is:

1. An ultrasound imaging system providing automatic activation of a probe, which ultrasound system comprises:

motion sensor means for detecting motion of the probe and for generating a signal in response to the motion;

signal detecting means for detecting the signal; and probe activating means for activating the probe in response to a detector signal from the detecting means;

wherein:

the motion sensor means is affixed to the probe and comprises an accelerometer, and the signal detecting means provides information identifying the probe to the probe activating means, which information is contained in the detector signal.

2. An ultrasound imaging system having a main control station and one or more probes and providing automatic activation of the one or more probes, which ultrasound system comprises:

motion sensor means for detecting motion of the one or more probes and for generating a motion signal in response to the motion;

probe activating means for activating the probes in response to the motion signal;

the motion sensor means in turn comprising:
a probe motion sensor for, and affixed to, each of at least one of the probes and;
a motion sensing controller affixed to the main control station.

3. An ultrasound imaging system as defined in claim 2, further including signal detection means for identifying the probe to be activated and for generating the motion signal in response to any signals generated by the motion sensing controller or any probe motion sensor.

4. An ultrasound imaging system providing automatic activation of a probe, which ultrasound system comprises:

motion sensor means for detecting motion of the probe and for generating a signal in response to the motion;

signal detecting means for detecting the signal; and probe activating means for activating the probe in response to a detector signal from the signal detecting means;

wherein the signal provides information identifying the probe.

5. The ultrasound imaging system of claim 4 wherein the signal detecting means provides the identifying information to the activating means in the detector signal.

6. An ultrasound imaging system providing automatic probe activation, the ultrasound system comprising:

a plurality of probes;

for each of at least two of the probes, a motion sensor affixed to the respective probe and generating a motion signal in response to motion of the corresponding probe;

a signal detector detecting the motion signal from each motion sensor; and probe activating means for selectively activating the probes in response to a detector signal from the signal detector;

the signal detector providing information to the probe activating means identifying as an active probe one of the probes in motion, which information is contained in the detector signal.

\* \* \* \* \*